United States Patent
Kergosien et al.

(10) Patent No.: US 10,639,256 B2
(45) Date of Patent: *May 5, 2020

(54) NON-TACKY PHOTOCROSSLINKABLE COSMETIC COMPOSITION

(71) Applicant: L'OREAL, Paris (FR)

(72) Inventors: Guillaume Kergosien, Chaville (FR); Carl Riachi, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/648,152

(22) PCT Filed: Dec. 4, 2013

(86) PCT No.: PCT/EP2013/075549
§ 371 (c)(1),
(2) Date: May 28, 2015

(87) PCT Pub. No.: WO2014/086872
PCT Pub. Date: Jun. 12, 2014

(65) Prior Publication Data
US 2015/0297487 A1 Oct. 22, 2015

Related U.S. Application Data

(60) Provisional application No. 61/754,102, filed on Jan. 18, 2013.

(30) Foreign Application Priority Data

Dec. 5, 2012 (FR) ..................... 12 61686

(51) Int. Cl.
*A61K 8/44* (2006.01)
*A61Q 3/02* (2006.01)
*A61K 8/73* (2006.01)
*A45D 29/04* (2006.01)
*A45D 29/18* (2006.01)
*A45D 31/00* (2006.01)
*A61K 8/45* (2006.01)
*A61K 8/40* (2006.01)

(52) U.S. Cl.
CPC ............... *A61K 8/44* (2013.01); *A45D 29/04* (2013.01); *A45D 29/18* (2013.01); *A45D 31/00* (2013.01); *A61K 8/40* (2013.01); *A61K 8/45* (2013.01); *A61K 8/731* (2013.01); *A61Q 3/02* (2013.01); *A61K 2800/81* (2013.01); *A61K 2800/95* (2013.01)

(58) Field of Classification Search
None
See application file for complete search history.

(56) References Cited

U.S. PATENT DOCUMENTS

| 6,015,549 A | 1/2000 | Copperthwaite |
| 2006/0191553 A1 | 8/2006 | Anderson et al. |
| 2010/0012548 A1 | 1/2010 | McClanahan |
| 2011/0060065 A1 | 3/2011 | Vu et al. |
| 2011/0081306 A1 | 4/2011 | Vu et al. |
| 2011/0082228 A1 | 4/2011 | Vu et al. |
| 2011/0226271 A1 | 9/2011 | Raney et al. |
| 2012/0118314 A1* | 5/2012 | Haile .......... A45D 34/045 132/200 |

(Continued)

FOREIGN PATENT DOCUMENTS

| DE | 102011102661 A1 | 11/2012 |
| FR | 2972634 A1 | 9/2012 |
| RU | 2 188 625 C1 | 9/2002 |

(Continued)

OTHER PUBLICATIONS

Tom Barclift: "Esstech, Imc. UV Nail Gel Products", Nov. 8, 2011.
U.S. Appl. No. 61/662,988, filed Jun. 22, 2012, Lein.
U.S. Appl. No. 61/696,931, filed Sep. 5, 2012, Lein.
U.S. Appl. No. 61/807,075, filed Apr. 1, 2013, Lein.
Tom Barclift: "Esstech, Inc. UV Nail Gel Products", Nov. 8, 2011.
Aniruddhans: "Esstech, Inc.—Product Catalog", Jun. 7, 2012.
Patil, A.A. Nail Care: The science that stands behind nail lacquers. Household and Person Care Today. Jan. 2008.

(Continued)

*Primary Examiner* — Nicole P Babson
(74) *Attorney, Agent, or Firm* — Polsinelli PC

(57) ABSTRACT

The present invention relates to a photocrosslinkable cosmetic composition, comprising in a physiologically acceptable medium: —at least one photocrosslinkable urethane (meth)acrylate compound P1 comprising at least one structural unit: (I) —at least one photocrosslinkable urethane (meth)acrylate compound P2 comprising at least one polyether chain, said compound having a molar mass greater than or equal to 1000 g/mol, —at least one film-forming polymer P3, —at least one photoinitiator, and —at least one volatile solvent chosen from acetone, ethyl acetate, and propyl acetate, said solvent being present in said composition at a content greater than or equal to 20%, preferably greater than or equal to 30%, by weight in relation to the total weight of said composition, wherein the ratio of the total mass of P1 and P2 to the total mass of P3 is less than or equal to 4.0.

(I)

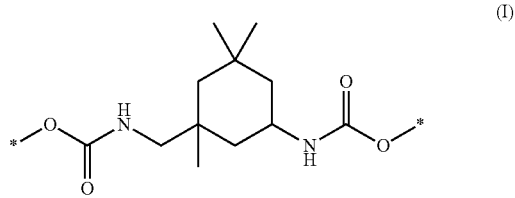

8 Claims, No Drawings

(56) References Cited

U.S. PATENT DOCUMENTS

2015/0335568 A1* 11/2015 Lein .................. A61Q 3/02
424/61

FOREIGN PATENT DOCUMENTS

| WO | WO-2011/011304 A2 | 1/2011 |
| WO | WO-2011/011304 A3 | 1/2011 |
| WO | WO-2011/011304 A8 | 1/2011 |
| WO | WO-2011/031578 A1 | 3/2011 |

OTHER PUBLICATIONS

International Search Report, International Application No. PCT/EP2013/075560, dated Nov. 9, 2014.
Exothane Elastomers. http://catalog.esstechinc.com/Asset/Exothane%20Comparison%20Chart%20EXO%20025%20v%2009%2024.pdf available Sep. 25, 2011; accessed Jul. 19, 2016.
Zanchi et al., "A new approach in self-etching adhesive formulations: Replacing HEMA for surfactant dimethacrylate monomers", J. of Biomedical Materials Res. Part B: Applied Biomaterials, Oct. 2011.
Esstech, Inc. Exothane™ Elastomers; Jul. 19, 2017.
Munchow et al., "Effect of elastomeric monomers as polymeric matrix of experimental adhesive systems: degree of conversion and bond strength characterization", Applied Adhesion Science 2014, 2:3.

* cited by examiner

NON-TACKY PHOTOCROSSLINKABLE COSMETIC COMPOSITION

CROSS REFERENCE TO RELATED APPLICATIONS

This application is a National Phase filing under 35 U.S.C. § 371 of PCT/EP2013/075549 filed on Dec. 4, 2013; and this application claims priority to Application No. 1261686 filed in France on Dec. 5, 2012, and this application claim the benefit of U.S. Provisional Application No. 61/754,102 filed on Jan. 18, 2013. The entire contents of each application are hereby incorporated by reference.

The present invention relates to a photocrosslinkable cosmetic composition, particularly for nail and/or false nail makeup and/or care.

More particularly, the present invention relates to a photocrosslinkable nail varnish composition.

The present invention also relates to a nail and/or false nail makeup and/or care method using said composition.

Nail varnish compositions may be used as a base for the varnish (or base-coat), as a nail makeup product, or as a finishing composition (or top-coat) to be applied on the nail makeup product, or as a cosmetic nail care product. These compositions may be applied onto natural nails as well as onto false nails.

In the field of nail varnishes, liquid cosmetic compositions are known, which are used by first applying a coat onto the nail and then subjecting said coat to the action of light radiation, inducing in situ polymerization and/or crosslinking reactions within said coat, resulting in generally crosslinked polymeric networks. Such photocrosslinkable compositions, commonly referred to as "UV gels" and generally based on crosslinkable (meth)acrylate compounds, are suitable for obtaining a satisfactory stability of the coat applied on the nail, and are described for example in CA 1 306 954, U.S. Pat. Nos. 5,456,905, 7,375,144 and FR 2 823 105.

However, the oxygen in air induces the inhibition of the radical polymerization and/or crosslinking reaction on the coat surface in contact with air, resulting in the formation of a tacky layer of unreacted (meth)acrylate compounds on the surface of said coat. Following the crosslinking step, cleaning of the coat surface with isopropanol for example (commonly referred to as "degreasing") is thus necessary to remove said tacky layer. This represents a drawback since it adds an additional step for nail or false nail makeup.

Moreover, if the tacky layer is not cleaned properly, sensitizing unreacted (meth)acrylate compounds may remain on the nails, false nails and skin.

The aim of the present invention is to provide a novel photocrosslinkable composition having satisfactory rigidity, stability and gloss properties, which is easy to use, but does not have the drawbacks of the photocrosslinkable cosmetic compositions according to the prior art.

In particular, the aim of the present invention is to provide a photocrosslinkable composition not having a tacky surface after the crosslinking step.

Another aim of the present invention is to provide a photocrosslinkable composition comprising a low proportion of sensitizing (meth)acrylate compounds.

Another aim of the invention is to obtain photocrosslinkable compositions suitable for providing coats having the following properties: stability over time (with a mild etching or without any etching of the nail or false nail before applying the composition), easy makeup removal, high cosmeticity, outstanding makeup result (homogeneous deposition, easy to apply, comfortable to wear) and/or high gloss.

The present invention relates to a photocrosslinkable cosmetic composition, comprising in a physiologically acceptable medium:
  at least one photocrosslinkable urethane (meth)acrylate compound P1 comprising at least one structural unit:

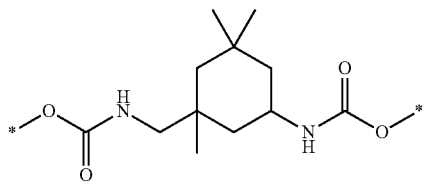

at least one photocrosslinkable urethane (meth)acrylate compound P2 comprising at least one polyether chain, said compound having a molar mass greater than or equal to 1000 g/mol,
  at least one film-forming polymer P3,
  at least one photoinitiatorphotoinitiator, and
  at least one volatile solvent chosen from acetone, ethyl acetate, and propyl acetate, said solvent being present in said composition at a content greater than or equal to 20%, preferably greater than or equal to 30%, by weight in relation to the total weight of said composition,
wherein the proportion of (meth)acrylate monomers is preferably less than or equal to 10% by weight in relation to the total weight of said composition, and wherein the ratio of the total mass of P1 and P2 to the total mass of P3 is less than or equal to 4.0.

The cosmetic compositions according to the invention comprise a physiologically acceptable medium.

The term "physiologically acceptable medium" refers to a medium that is particularly suitable for the application of a composition of the invention onto keratin matter.

The physiologically acceptable medium is generally suitable for the nature of the support to which the composition should be applied, and also for the way in which the composition is to be packaged.

The term "(meth)acrylate monomer" refers to a compound comprising a single (meth)acrylate function according to the formula $H_2C{=}C(R){-}C(O){-}O{-}$, where $R{=}H$ or $CH_3$.

According to one embodiment, the photocrosslinkable composition according to the invention comprises a reduced proportion of (meth)acrylate monomers, i.e. less than 10% by weight in relation to the total weight of said composition. Preferably, this proportion is less than or equal to 5%, preferentially less than or equal to 1% by weight. Advantageously, the composition according to the invention is completely free from (meth)acrylate monomer.

The term "photocrosslinkable compound" refers to an organic compound suitable for crosslinking under the action of a light ray, resulting in a crosslinked polymer network.

Preferably, the film-forming polymer P3 is a non-photocrosslinkable compound.

The term "non-photocrosslinkable compound" refers to a compound inert to any light exposure, i.e. that does not polymerize and/or is not crosslinked, unlike the photocrosslinkable compounds P1 and P2.

In particular, the film-forming polymer P3 is generally free from double ethylene bonds, such as (meth)acrylate groups.

In the composition according to the invention, the ratio of the total mass of P1 and P2 to the total mass of P3 is less than or equal to 4.0.

Surprisingly, the inventors observed that a photocrosslinkable composition according to the invention comprising the combination of the compounds P1 and P2 and the film-forming polymer P3, observing the mass ratio defined above, is suitable for obtaining a crosslinked coat, consisting of said photocrosslinkable composition, not having a tacky surface, but having satisfactory rigidity, stability and gloss properties, however.

Without seeking to be associated with a particular theory, the inventors observed that, once crosslinked, the photocrosslinkable compound P1 makes it possible to increase the rigidity of said coat.

In the composition according to the invention, the mass ratio between P1 and P2 typically ranges from 0.5 to 2.5, preferably from 1.0 to 2.0, advantageously from 1.25 to 1.75.

Urethane (Meth)Acrylate Compound

The term "urethane (meth)acrylate compound" refers to any compound comprising at least one urethane function —O—C(O)—NH—, and at least one (meth)acrylate function according to the formula $H_2C=C(R)-C(O)-O-$, where R=H or $CH_3$.

The "urethane" function is also referred to as a "carbamate" function.

Photocrosslinkable Compound P1

The composition according to the invention comprises at least one first photocrosslinkable compound, referred to as P1, which is a urethane (meth)acrylate compound and which comprises at least one structural unit:

The photocrosslinkable compound P1 preferably is of general formula:

where $R_i$ and $R_{ii}$ are identical or different groups, each representing a $C_1$-$C_6$ alkyl group substituted with one or a plurality of (meth)acrylate groups, or a polyurethane group, comprising 2 to 20 urethane units, said polyurethane being substituted by one or a plurality of (meth)acrylate groups.

The term "polyurethane group" refers to a group obtained from polymerizing a mixture of monomers comprising isocyanate functions and monomers comprising alcohol functions.

According to one embodiment, the photocrosslinkable compound P1 is chosen from the group consisting of urethane poly(meth)acrylate compounds, advantageously in the group consisting of urethane di(meth)acrylate compounds, preferably in the group consisting of urethane dimethacrylate compounds.

According to the present invention, the term "poly(meth)acrylate compound" refers to a (meth)acrylate compound comprising a plurality of (meth)acrylate functions.

In this way, the term "poly(meth)acrylate compound" may refer to a compound comprising at least two methacrylate functions, or at least two acrylate functions, or at least one methacrylate function and at least one acrylate function.

Preferably, the photocrosslinkable compound P1 is a urethane dimethacrylate compound.

The term "urethane dimethacrylate compound" refers to any compound comprising at least one urethane function —O—C(O)—NH—, and two methacrylate functions according to the formula $H_2C=C(CH_3)-C(O)-O-$.

According to another embodiment, the photocrosslinkable compound P1 is of formula:

wherein:
- j is an integer ranging from 1 to 10, preferably equal to 2,
- R1 and R2, identical or different, represent a hydrogen atom or a methyl group,
- R3 and R4, identical or different, represent a hydrogen atom or a $C_1$-$C_{10}$ alkyl chain, preferably a hydrogen atom or a methyl group, and
- -A- represents a linear or branched $C_1$-$C_{10}$ divalent alkylene group, or a divalent polyurethane group, comprising from 2 to 20 urethane units.

Preferably, R1 and R2 are methyl groups.

According to another embodiment, the photocrosslinkable compound P1 is of formula (I):

(I)

wherein:
i is an integer ranging from 1 to 6, preferably equal to 2,
j is an integer ranging from 1 to 6, preferably equal to i, and preferentially equal to 2, and
R3 and R4, identical or different, represent a hydrogen atom or a $C_1$-$C_{10}$ alkyl chain, preferably a hydrogen atom or a methyl group.

The photocrosslinkable compound P1 preferably has a dynamic viscosity greater than or equal to 20 Pa·s, preferably less than or equal to 50 Pa·s at 20° C.

The dynamic viscosity of the photocrosslinkable compound P1 may be measured using a Brookfield rotary viscometer, according to the conventional method specified in the instructions provided by the manufacturer.

The composition according to the invention optionally comprises a mixture of different compounds P1.

The compound(s) P1 is (are) preferably present at a total content greater than or equal to 1% by weight, in relation to the total weight of the photocrosslinkable composition, advantageously ranging from 1 to 20%, preferably from 5 to 15%, preferably from 10 to 15% by weight in relation to the total weight of the photocrosslinkable composition.

As an example of a suitable photocrosslinkable compound P1, mention may be made of Isophorone Urethane Dimethacrylate (X-851-1066—ESSTECH, Inc.).

Photocrosslinkable Compound P2

The composition according to the invention comprises at least one second photocrosslinkable compound, referred to as P2, which is a urethane (meth)acrylate compound and comprises a polyether chain.

Advantageously, the mean number of (meth)acrylate functions borne by the photocrosslinkable compounds P2 intended to form, after crosslinking, a crosslinked polymeric network, is greater than 1. Indeed, a polymerizable system consisting of molecules each bearing a single (meth)acrylate function forms, after reacting all of said functions, a linear or branched, and not crosslinked, chain macromolecular system. Only the presence of a certain fraction of molecules bearing at least two (meth)acrylate functions and thus acting as a crosslinking agent is suitable for obtaining a crosslinked polymeric system.

In the implementation of the present invention, the mean number of (meth)acrylate functions per molecule of compound P2 is preferably greater than or equal to 2, advantageously ranging from 2 to 6, preferably from 2 to 4.

Preferentially, P2 is a urethane dimethacrylate compound.

The term "urethane dimethacrylate compound" refers to any compound comprising at least one urethane function —O—C(O)—NH—, and two methacrylate functions according to the formula $H_2C=C(CH_3)$—C(O)—O—.

Polyether Chain

The term "polyether chain" refers to a $C_1$-$C_{100}$ divalent hydrocarbon radical, interspersed with at least two oxygen atoms.

Preferably, the polyether chain of the compound P2 has a molar mass less than or equal to 1000 g/mol.

Preferentially, the polyether chain generally comprises less than 50 carbon atoms, preferably less than 45 carbon atoms.

According to one alternative embodiment, the polyether chain of the P2 photocrosslinkable compound P2 is of formula —$[C_nH_2O]_m$—, wherein n is an integer ranging from 1 to 6, preferably equal to 2 or 3, and m is an integer ranging from 2 to 50.

It may thus consist for example of a polyoxymethylene chain according to the formula —$[CH_2O]_m$—, a poly(ethyleneglycol) chain according to the formula —$[CH_2CH_2O]_m$—, a poly(propyleneglycol) chain according to the formula —$[CH_2CH(CH_3)O]_m$— or a polytetramethyleneglycol chain according to the formula —$[(CH_2)_4O]_m$—.

According to one preferred embodiment of this alternative embodiment, the polyether chain is such that n=2 and m ranges from 2 to 20, preferably from 5 to 20.

According to a further alternative embodiment, the polyether chain of the photocrosslinkable compound P2 is of formula —$[PhO]_m$—, wherein Ph refers to a phenylene divalent radical, optionally substituted with one or a plurality of $C_1$-$C_6$ alkyls and/or halogen atoms, and m is an integer ranging from 2 to 50.

It may thus consist for example of a polyphenylether chain according to the formula —$[C_6H_4O]_m$— or a poly(p-dimethylphenyl)ether chain according to the formula —$[(C_6H_2)(CH_3)_2O]_m$—.

According to one alternative embodiment, the photocrosslinkable compound P2 is of formula (II):

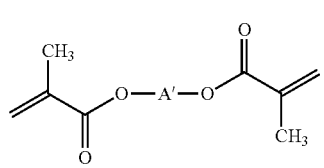

(II)

wherein -A'- represents a $C_1$-$C_{100}$ divalent hydrocarbon radical, optionally substituted with alkyl groups, said radical being interspersed with at least one urethane function —O—C(O)—NH—, at least one polyether chain as defined above, and optionally with heteroatoms, such as oxygen, nitrogen, sulfur atoms, or saturated, aromatic or heteroaromatic cyclic divalent groups, such as cycloalkylene, arylene or heteroarylene groups.

Within the scope of the present invention, the heteroatoms include oxygen, nitrogen and sulfur atoms.

According to the present invention, the "alkyl" groups represent straight or branched chain saturated hydrocarbon radicals, comprising from 1 to 10 carbon atoms, preferably from 1 to 6 carbon atoms. Mention may particularly be made, when they are linear, of methyl, ethyl, propyl, butyl, pentyl, hexyl, octyl, nonyl and decyl radicals. Mention may particularly be made, when they are branched or substituted with one or a plurality of alkyl radicals, of isopropyl, tert-butyl, 2-ethylhexyl, 2-methylbutyl, 2-methylpentyl, 1-methylpentyl and 3-methylheptyl radicals.

The "cycloalkene" radical is a non-aromatic saturated or partially unsaturated mono-, bi- or tri-cyclic divalent hydrocarbon radical, comprising from 3 to 20 carbon atoms, and preferably from 3 to 10 carbon atoms, such as in particular cyclopropylene, cyclopentylene, cyclohexylene or adamantylene, optionally substituted with alkyl groups, and the corresponding rings containing one or a plurality of unsaturations.

In this way, within the scope of the present invention, the term "cycloalkylene" also covers "heterocycloalkylene" radicals denoting non-aromatic saturated or partially unsaturated mono- or bicyclic divalent radicals, of 3 to 8 carbon atoms, comprising one or a plurality of heteroatoms chosen from N, O or S.

The term "arylene" refers to a mono or bicyclic aromatic divalent hydrocarbon radical, comprising from 6 to 30, preferably from 6 to 10, carbon atoms. Of the arylene radicals, mention may particularly be made of the phenylene or naphthylene radical, more particularly substituted with at least one halogen atom.

If the arylene radical comprises at least one heteroatom, the term "heteroarylene" radical is used. In this way, the term "heteroarylene" refers to an aromatic divalent radical comprising one or a plurality of heteroatoms chosen from nitrogen, oxygen or sulfur, comprising from 5 to 30, and preferably from 5 to 10, carbon atoms. Of the heteroarylene radicals, mention may be made of pyrazinylene, thienylene, oxazolylene, furazanylene, pyrrolylene, 1,2,4-thiadiazolylene, naphthyridinylene, pyridazinylene, quinoxalinylene, phtalazinylene, imidazo[1,2-a]pyridinene, imidazo[2,1-b]thiazolylene, cinnolinylene, triazinylene, benzofuranzanylene, azaindolylene, benzimidazolylene, benzothienylene, thienopyridylene, thienopyrimidinylene, pyrrolopyridylene, imidazopyridylene, benzoazaindolene, 1,2,4-triazinylene, benzothiazolylene, furanylene, imidazolylene, indolylene, triazolylene, tetrazolylene, indolizinylene, isoxazolylene, isoquinolinylene, isothiazolylene, oxadiazolylene, pyrazinylene, pyridazinylene, pyrazolylene, pyridylene, pyrimidinylene, purinylene, quinazolinylene, quinolinylene, isoquinolylene, 1,3,4-thiadiazolylene, thiazolylene, triazinylene, isothiazolylene, carbazolylene, along with the corresponding groups obtained from the fusion thereof or fusion with the phenyl nucleus.

According to a further alternative embodiment, the compound P2 is of formula (III):

The compound(s) P2 is (are) preferably present at a total content greater than or equal to 1% by weight, in relation to the total weight of the photocrosslinkable composition, advantageously ranging from 1 to 20%, preferably from 2 to 15%, preferably from 5 to 10% by weight in relation to the total weight of the photocrosslinkable composition.

The composition according to the invention optionally comprises a mixture of different compounds P2.

Film-Forming Polymer P3

The composition according to the invention comprises at least one film-forming polymer P3, different to the photocrosslinkable compound P1 and different to the photocrosslinkable compound P2.

The term "film-forming polymer" refers to, according to the invention, a polymer suitable for forming alone (i.e. in the absence of an auxiliary film-forming agent or an external stimulus for example such as UV), a film suitable for being isolated, particularly a continuous adherent film, on a substrate, particularly on nails.

A single film-forming polymer or a mixture of film-forming polymers may be used.

This film-forming polymer may be chosen from the group consisting of radical or polycondensate type synthetic polymers, polymers of natural origin, and mixtures thereof.

A film-forming polymer suitable for the invention may be chosen from polysaccharide derivatives, such as cellulose or guar gum derivatives. One preferential polysaccharide

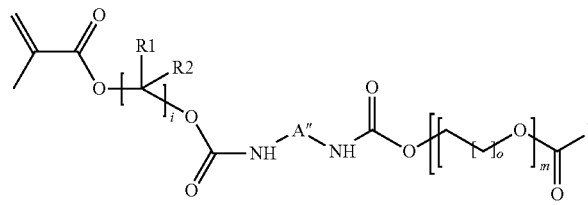
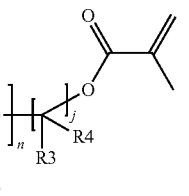
(III)

wherein:
i is an integer ranging from 1 to 6, preferably equal to 2,
j is an integer ranging from 1 to 6, preferably equal to i, and preferentially equal to 2,
m is an integer ranging from 1 to 20,
n is an integer between 1 and 10, preferably equal to 1,
o is an integer between 1 and 10, preferably equal to 1,
R1, R2, R3 and R4, identical or different, represent a hydrogen atom or a $C_1$-$C_{10}$ alkyl chain, preferably a hydrogen atom or a methyl group, and
-A"- represents a linear or branched $C_1$-$C_{20}$, divalent hydrocarbon alkylene group, or a $C_5$-$C_{20}$ divalent cycloalkylene radical.

Preferably, -A"- represents a radical according to the formula:

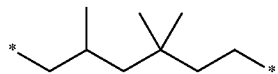 [SMILES: *CCC(C)(C)CC(C)C*]

A photocrosslinkable compound suitable for the implementation of the invention is for example PEG 400 Extended Urethane Dimethacrylate (X-726-0000—ES-STECH, Inc.).

derivative suitable for the invention may be nitrocellulose or a polysaccharide ester or alkylether.

The term "polysaccharide ester or alkylether" refers to a polysaccharide consisting of repeat units comprising at least two identical or different rings and having a degree of substitution per saccharide unit between 1.9 and 3, preferably between 2.2 and 2.9, and more particularly between 2.4 and 2.8. The term substitution refers to the functionalization of hydroxyl groups into ester and/or alkylether functions, and/or the functionalization of carboxyl groups into ester functions.

In other words, it may consist of a polysaccharide, partially or totally substituted with ester and/or alkylether groups. Preferably, the hydroxyl groups may be substituted with $C_2$-$C_4$ ester and/or alkylether functions.

Particular mention may be made of cellulose esters (such as cellulose acetobutyrates or cellulose acetopropionates), cellulose alkylethers (such as ethylcelluloses), and ethylguars.

A film-forming polymer suitable for the invention may be chosen from synthetic polymers such as polyurethanes, acrylic polymers, vinyl polymers, polyvinylbutyrals, alkyd resins and ketone/aldehyde resins, resins from aldehyde condensation products, such as aryl sulfonamide formaldehyde resins such as toluene sulfonamide formaldehyde resin, aryl-sulfonamide epoxy resins or ethyl tosylamide resins.

In particular, it may consist of (meth)acrylate homopolymers and copolymers.

A film-forming polymer suitable for the invention may also be chosen from polymers of natural origin, such as plant resins such as dammars, elemi, copals, benzoin; gums such as shellac, sandarac and mastic.

As a film-forming polymer, the toluene sulfonamide formaldehyde resins "Ketjentflex MS80" from AKZO or "Santolite MHP", "Santolite MS 80" from FACONNIER or "RESIMPOL 80" from PAN AMERICANA, the alkyd resin "BECKOSOL ODE 230-70-E" from DAINIPPON, the acrylic resin "ACRYLOID B66" from ROHM & HAAS, the polyurethane resin "TRIXENE PR 4127" from BAXENDEN, the acetophenone/formaldehyde resin marketed under the reference Synthetic Resin SK by Degussa may notably be used.

According to one preferred particular embodiment, the film-forming polymer P3 is chosen from polysaccharides and polysaccharide derivatives, preferably from nitrocellulose and polysaccharide ethers and esters, particularly $C_2$-$C_4$, and more preferentially from cellulose acetobutyrates, cellulose acetopropionates, ethylcelluloses, ethylguars, and mixtures thereof.

According to one particularly preferred embodiment, the film-forming polymer P3 is chosen from nitrocellulose, cellulose acetopropionate, cellulose acetobutyrate, and (meth)acrylate homopolymers and copolymers.

Advantageously, the film-forming polymer P3 is nitrocellulose.

The compositions according to the invention optionally comprise a mixture of different film-forming polymers P3.

According to one embodiment, in the composition according to the invention, the ratio of the total mass of P1 and P2 to the total mass of P3 is less than or equal to 2.5, preferably ranging from 0.25 to 2.5, preferentially ranging from 0.5 to 2.0.

Photoinitiator

The composition according to the invention comprises at least one photoinitiator.

The photoinitiators suitable for use according to the present invention are known in the art and are described, for example in "Les photoinitiateurs dans la réticulation des revetements", G. Li Bassi, Double Liaison—Chimie des Peintures, No. 361, November 1985, p. 34-41; "Applications industrielles de la polymérisation photoinduite", Henri Strub, L'Actualité Chimiqué, February 2000, p. 5-13; and "Photopolymères: considérations théoriques et réaction de prise", Marc, J. M. Abadie, Double Liaison—Chimie des Peintures, No. 435-436, 1992, p. 28-34.

These photoinitiators include:
α-hydroxyketones, marketed for example under the names DAROCUR® 1173 and 4265, IRGACURE® 184, 2959, and 500 by BASF, and ADDITOL® CPK by CYTEC,
α-aminoketones, marketed for example under the names IRGACURE® 907 and 369 by BASF,
aromatic ketones marketed for example under the name ESACURE® TZT by LAMBERTI. Mention may also be made of thioxanthones marketed for example under the name ESACURE® ITX by LAMBERTI, and quinones. These aromatic ketones generally require the presence of a hydrogen donor compound such as tertiary amines and particularly alkanolamines. Mention may particularly be made by the tertiary amine ESACURE® EDB marketed by LAMBERTI.
α-dicarbonyl derivatives of which the most common is benzyl dimethyl ketal marketed under the name IRGACURE® 651 by BASF. Further commercial products are marketed by LAMBERTI under the name ESACURE® KB1, and
acylphosphine oxides, such as for example bis-acylphosphine oxides (BAPO) marketed for example under the names IRGACURE® 819, 1700, and 1800, DAROCUR® 4265, LUCIRIN® TPO, and LUCIRIN® TPO-L by BASF.

Preferably, the photoinitiator of the composition according to the invention is chosen from the group consisting of α-hydroxyketones, α-aminoketones, aromatic ketones preferably associated with a hydrogen donor compound, aromatic α-diketones, acylphosphine oxides, and mixtures thereof.

Preferably, the photoinitiator of the composition according to the invention is chosen from acylphosphine oxides, such as for example LUCIRIN® TPO-L (BASF), α-hydroxyketones, such as for example IRGACURE® 184 (BASF), and mixtures thereof.

A mixture of photoinitiators absorbing light radiation at various wavelengths may also be used in the photocrosslinkable composition according to the invention. The absorption spectrum of the photocrosslinkable composition can thus be adapted to the emission spectrum of the light sources used.

Preferably, the composition according to the invention comprises a mixture of two different photoinitiators, such as for example a mixture of an α-hydroxyketone and an acylphosphine oxide.

A particular group of photoinitiators suitable for use in the photocrosslinkable cosmetic compositions according to the present invention is that of copolymerizable photoinitiators. It consists of molecules comprising both a photoinitiator group capable of photoinduced radical splitting and at least one double ethylene bond. The photoinitiators in this group offer the advantage, in relation to the conventional photoinitiators listed above, of being suitable for being incorporated, via the double bond, into the macromolecular system. This possibility reduces the content of free residual photoinitiators not having undergone photoinduced radical splitting and thus enhances the safety of the layer C1.

As examples of such copolymerizable photoinitiators, mention may be made of benzophenone acrylate derivatives marketed by CYTEC under the names EBECRYL® P36, EBECRYL® P37.

In one preferred embodiment of the invention, polymer photoinitiators or photoinitiators bound onto a high molar mass molecule are used. The choice of such a high mass photoinitiator offers the same advantage as selecting only polymeric copolymerizable compounds, i.e. enhanced safety of the photocrosslinkable cosmetic compositions due to the absence of very reactive molecules liable to diffuse to neighboring biological substrates. The mean molar mass by weight of the photoinitiator is preferably at least equal to 500 g/mol.

For example, mention may be made of an α-hydroxyketone oligomer corresponding to the following formula:

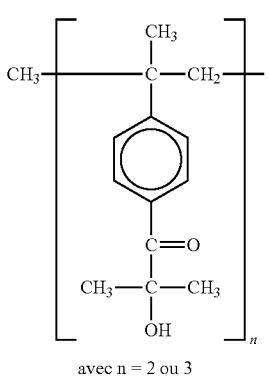

avec n = 2 ou 3 and which is marketed under the name ESACURE® KIP 150 by LAMBERTI.

The polymer on which the photoinitiator group is bound may optionally comprise one or a plurality of double ethylene bonds for optionally incorporating, into the macromolecular network, photoinitiator molecules not having undergone photoinduced splitting.

As examples of such high molar mass photoinitiators bearing double ethylene bonds, mention may be made of those corresponding to the following formulae:

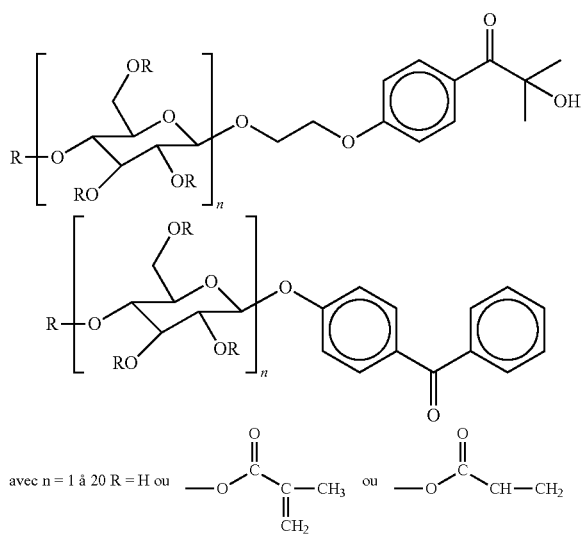

avec n = 1 á 20 R = H ou

These structures are described in the following articles: S. Knaus, Pure Appl. Chem., A33(7), 869 (1996); S. Knaus, J. Polym. Sci, Part A=Polym. Chem., 33, 929 (1995); and R. Liska, Rad'Tech Europe 97, Lyon, F, 1997, Conference Proceedings.

The content of the photoinitiator(s) used is dependent on a large number of factors such as the reactivity of the various constituents of the mixture, the presence of pigments or dyes, the crosslinking density sought, the intensity of the light source or the exposure time.

In order to obtain satisfactory mechanical properties, the photoinitiator(s) is (or are) preferably present in a total content greater than or equal to 0.1% by weight in relation to the total weight of the photocrosslinkable composition, preferably from 1 to 5% by weight in relation to the total weight of the photocrosslinkable composition.

Preferably, the photoinitiator(s) is (or are) present in a total content greater than or equal to 0.1% by weight in relation to the total weight of the photocrosslinkable compound(s), preferably from 1% to 15% by weight in relation to the total weight of the photocrosslinkable compound(s) P1 and P2.

Solvents

The composition according to the present invention generally comprises at least one solvent chosen from physiologically acceptable organic and inorganic solvents.

The suitable solvents may particularly be chosen from:
liquid ketones at ambient temperature such as methylethylketone, methylisobutylketone, diisobutylketone, isophorone, cyclohexanone and acetone,
liquid alcohols at ambient temperature such as ethanol, isopropanol, diacetone-alcohol, 2-butoxyethanol and cyclohexanol,
liquid glycols at ambient temperature such as ethyleneglycol, propyleneglycol, pentyleneglycol and glycerol,
liquid propyleneglycol ethers at ambient temperature such as propyleneglycol monomethylether, propyleneglycol monomethyl ether acetate and dipropyleneglycol mono-n-butylether,
short-chain esters (comprising in total from 3 to 8 carbon atoms) such as ethyl acetate, methyl acetate, propyl acetate, n-propyl acetate, iso-propyl acetate, n-butyl acetate, iso-butyl acetate, ter-butyl acetate and isopentyl acetate,
liquid alkanes at ambient temperature such as decane, heptane, dodecane and cyclohexane,
liquid aromatic hydrocarbons at ambient temperature such as toluene and xylene,
liquid silicones at ambient temperature, and
mixtures thereof.

The composition according to the invention preferably comprises so-called volatile solvents.

The term "volatile solvent" refers to a solvent capable of evaporating on contact with keratin matter, in less than one hour, at ambient temperature and at atmospheric pressure.

The volatile solvent(s) according to the invention are liquid solvents at ambient temperature, having a vapor pressure different to zero, at ambient temperature and atmospheric pressure, particularly ranging from 0.13 Pa to 40,000 Pa (from $10^{-3}$ to 300 mm Hg), particularly ranging from 1.3 Pa to 13,000 Pa (from 0.01 to 100 mm Hg), and more specifically ranging from 1.3 Pa to 1300 Pa (from 0.01 to 10 mm Hg).

On the other hand, a "non-volatile solvent" evaporates on contact with keratin matter in more than one hour, at ambient temperature and atmospheric pressure.

The total solvent content in the composition may range from 5% to 95% by weight, in relation to the total weight of the composition.

According to one embodiment, the volatile solvent content in the composition ranges from 30% to 80%, preferably from 50% to 70% in relation to the total weight of said composition.

Preferably, the composition comprises a solvent chosen from liquid alcohols at ambient temperature, such as ethanol and isopropanol, and short-chain esters comprising in total from 3 to 8 carbon atoms, such as ethyl acetate and butyl acetate, and mixtures thereof.

Preferably, the solvent of the composition according to the invention is ethyl acetate.

Adjuvants

According to one embodiment, the composition according to the invention further comprises a coloring agent chosen from the group consisting of soluble dyes, pigments, nacres and glitter.

The coloring agent(s) may be present in a total content greater than or equal to 0.1% by weight in relation to the total weight of the layer, ranging preferably from 0.1 to 5%, advantageously from 0.2 to 1% by weight in relation to the total weight of the layer.

The term "soluble dyes" should be understood to refer to organic, inorganic or organometallic compounds, soluble in the composition according to the invention and intended to color said composition.

The dyes are, for example, Sudan Red, DC Red 17, DC Green 6, βcarotene, soybean oil, Sudan Brown, DC Yellow 11, DC Violet 2, DC Orange 5, and Quinoline Yellow.

The term "pigments" should be understood to refer to inorganic or organic, white or colored particles of any shape, insoluble in the composition according to the invention and intended to color said composition.

The term "nacres" should be understood to refer to iridescent particles of any shape, particularly produced by some mollusks in their shell or by synthetic means.

The pigments may be white or colored, inorganic and/or organic. Of the inorganic pigments, mention may be made of titanium dioxide, optionally surface-treated, zirconium or cerium oxides, along with zinc, iron (black, yellow or red) or chromium oxides, manganese violet, ultramarine blue, chromium hydrate and iron blue, metallic powders such as aluminum powder, copper powder.

Of the organic pigments, mention may be made of carbon black, D & C type pigments, and lacquers based on cochineal carmine, barium, strontium, calcium, aluminum.

Mention may also be made of effect pigments such as particles comprising a natural or synthetic organic or inorganic substrate, for example glass, acrylic resins, polyester, polyurethane, polyethylene terephthalate, ceramics, aluminas and optionally coated with metallic substances such as aluminum, gold, copper, bronze, or with metal oxides such as titanium dioxide, iron oxide, chromium oxide, inorganic or organic pigments and mixtures thereof.

The pearlescent pigments may be chosen from white pearlescent pigments such as mica coated with titanium, or bismuth oxychloride, colored pearlescent pigments such as titanium mica coated with iron oxides, titanium mica coated with iron blue and chromium oxide in particular, titanium mica coated with an organic pigments of the aforementioned type and pearlescent pigments based on bismuth oxychloride.

Pigments with goniochromatic properties may be used, particularly liquid crystal or multilayer pigments.

Optical brighteners or fibers optionally coated with optical brighteners may also be used.

The composition according to the invention may further comprise one or a plurality of fillers, particularly at a content ranging from 0.01% to 50% by weight, in relation to the total weight of the composition, preferably ranging from 0.01% to 30% by weight.

The term "fillers" should be understood to refer to inorganic or synthetic colorless or white particles of any shape, insoluble in the medium of the composition regardless of the temperature at which the composition is manufactured. These fillers may particularly be used to modify the rheology or texture of the composition.

The fillers may be mineral or organic particles of any shape, in sheet, spherical or oblong form, regardless of the crystallographic shape (for example sheet, cubic, hexagonal, orthorhombic, etc). Mention may be made of talc, mica, silica, kaolin, polyamide (Nylon®) (Orgasol® from Atochem), poly-alanine and polyethylene powders, tetrafluoroethylene polymer powders (Teflon®), lauroyl-lysine, starch, boron nitride, polymeric hollow microspheres such as those of polyvinylidene chloride/acrylonitrile like Expancel® (Nobel Industrie), acrylic acid copolymers (Polytrap® from Dow Corning) and silicone resin microbeads (Tospearls® from Toshiba, for example), elastomer polyorganosiloxane particles, precipitated calcium carbonate, magnesium carbonate and hydro-carbonate, hydroxyapatite, hollow silica microspheres (Silica Beads® from Maprecos), glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate.

The composition according to the invention may also further comprise adjuvants, or additives, particularly chosen from plasticizers, coalescing agents, preservatives, waxes, thickeners, perfumes, UV filters, cosmetic active substances for nail care, spreading agents, anti-foaming agents and dispersing agents.

Obviously, those skilled in the art will take care to choose these optional adjuvants or additives such that the advantageous properties of the composition according to the invention are not, or are practically not, altered by the envisaged addition.

If the composition comprises pigments and/or dyes, it is particularly advisable to adapt the absorption spectrum of the pigments and/or dyes used to that of the photoinitiators, or conversely the absorption spectrum of the photoinitiators to that of the pigments and/or dyes used, so as to prevent both types of compounds from absorbing light at the same wavelengths. Indeed, the absorption of light by the pigments and/or dyes would render the photoinitiators present beyond a specific depth of the coat almost completely ineffective.

Preferably, the composition according to the invention is transparent.

As used herein, the term transparent refers to that the composition has a HAZEBYK index of less than 5 as measured with a KYKHAZEGLOSS type gloss meter.

One particular composition according to the invention comprises, or consists of:
  from 1% to 20%, preferably from 10% to 15%, of a photocrosslinkable urethane dimethacrylate compound P1 according to formula (I) as defined above,
  from 1% to 20%, preferably from 5% to 10%, of a photocrosslinkable urethane dimethacrylate compound P2 comprising a poly(ethyleneglycol) chain,
  from 10% to 30%, preferably from 15% to 25%, of nitrocellulose,
  from 30% to 80%, preferably from 50% to 70%, of ethyl acetate, from 0.1% to 5%, preferably from 0.5% to 3.0%, of an acylphosphine oxide photoinitiator, an α-hydroxyketone photoinitiator, or of a mixture thereof, and optionally
  from 0.1% to 5% of a coloring agent,
  wherein the percentages are expressed in relation to the total weight of said composition.

The composition according to the invention is typically intended to be used as nail varnish.

As such, the present invention relates to a makeup and/or care method of a nail and/or false nail, comprising the following steps.
  a) applying, onto a nail or a false nail, a photocrosslinkable composition according to the invention, whereby a coat consisting of at least one layer of said photocrosslinkable composition is deposited, and
  b) exposing the coated nail or false nail obtained following step a) to UV or visible light radiation, whereby the photocrosslinking of the photocrosslinkable compounds P1 and P2 of said composition is carried out.

The radiation suitable for the crosslinking of the photocrosslinkable composition according to the present invention has a wavelength ranging from 210 to 600 nm, preferably from 250 to 420 nm, preferably from 350 to 410 nm. The use of lasers may also be envisaged.

In one preferred embodiment of the invention, a LED lamp or an UV lamp and particularly a mercury vapor lamp, optionally doped with further elements, such as gallium, suitable for modifying the emission spectrum of the light source, is used.

The exposure time of the deposited coat to radiation is dependent on various factors such as the chemical nature and content of the reactive compounds or the crosslinking density sought.

For nail varnishes, it would generally be sought to obtain satisfactory results for an exposure time ranging from 10 seconds to 10 minutes, preferably from 30 seconds to 5 minutes.

Such a method may use a UV lamp having a power of approximately 36 W.

Following the crosslinking step b), the coat deposited on the nail or false nail is not tacky and can be touched with a finger without leaving marks or damaging said coat. It is thus not necessary to perform any cleaning of the crosslinked coat, which saves time and facilitates use compared to the photocrosslinkable compositions currently on the market.

Preferably, the method according to the invention does not comprise a cleaning step after the crosslinking step b).

Without seeking to be associated with a particular theory, this lack of tack means that the surface of the coat is free from unreacted photocrosslinkable compounds which may be harmful for the adjacent or underlying nail substrates.

According to one embodiment, the method according to the invention further comprises, before step b), a period for drying the coat deposited following step a), the duration whereof may vary from 1 to 20 minutes, typically from 5 to 15 minutes. Said drying is generally performed in air and at ambient temperature.

A particular method according to the invention solely consists of a step a) and a step b) as defined above, optionally at an interval of a drying period as defined above.

According to one embodiment, after the crosslinking step b), the coat deposited on the nail is coated with at least one layer of a finishing composition, also known as a "top-coat", said finishing composition being optionally crosslinkable.

Preferably, the thickness after drying the coat of photocrosslinkable composition deposited in step a) is less than or equal to 100 µm, preferably less than or equal to 50 µm.

The crosslinked coat obtained from the crosslinking in step b) exhibits a significant stability over time, in terms of chipping resistance and gloss, particularly over the course of at least one week. It thus proves to be resistant to water, friction and shocks, and does not exhibit significant wear or chipping in this interval.

This coat is also capable of being solubilized or increasing in volume and thus weight when placed in contact with a standard makeup removal solvent. This ability to be solubilized or swell, displayed by the crosslinked coat, is specifically advantageous for the removal thereof when applied onto the surface of a nail or false nail. Indeed, the coat may be removed readily merely by means of makeup removal using a conventional solvent.

In this way, the composition according to the invention is advantageously suitable for being removed using standard solvents used in the field of nail varnish, and particularly using acetone and ethyl acetate, and mixtures thereof.

The present invention also relates to a makeup removal method of a nail and/or false nail, comprising the application of a makeup removal composition, such as a standard solvent described above, onto a nail or false nail coated with at least one layer obtained by crosslinking a layer of composition according to the invention, whereby said crosslinked layer is removed.

The present invention also relates to a kit comprising:
- a photocrosslinkable cosmetic composition according to the invention,
- an abrasive material having a granulometry greater than or equal to 200 µm, preferably less than 300 µm, advantageously comprised from 220 µm to 280 µm, and
- a LED lamp or an UV lamp.

The present invention also relates to a makeup and/or care method of a nail and/or false nail, comprising the following steps:
i) rubbing the surface of a nail or false nail with an abrasive material having a granulometry greater than or equal to 200 µm, preferably less than 300 µm, advantageously comprised from 220 µm to 280 µm,
ii) applying a photocrosslinkable composition according to the invention onto the surface of the nail or false nail which has been rubbed following step i), whereby a coat consisting of at least one layer of said photocrosslinkable composition is deposited, and
iii) exposing the coated nail or false nail obtained following step ii) to a LED lamp or an UV lamp, whereby the photocrosslinking of the photocrosslinkable composition is carried out.

Usually, the rubbing step is performed for less than 10 seconds, preferably less than 5 seconds, for example for approximately 3 seconds.

EXAMPLES

The present invention will now be illustrated using the following example.

A colored photocrosslinkable composition according to the invention (composition No. 1) is applied onto nails. After drying for approximately 10 minutes, the nail coated with the photocrosslinkable composition is then crosslinked for 60 seconds under an "OPI GelColor" lamp from OPI (wavelength: 404 nm).

Composition No. 1 (ratio (P1+P2)/P3=2 with 59% ethyl acetate)

| | |
|---|---|
| Isophorone Urethane Dimethacrylate (X-851-1066-ESSTECH, Inc.) | 13.5% |
| PEG 400 Extended Urethane Dimethacrylate (X-726-0000-ESSTECH, Inc.) | 9% |
| Nitrocellulose with 30% isopropyl alcohol (viscosity: E22-1/2s) | 16% |
| Ethyl acetate | 59% |
| Red 7 lacquer (Sunchroma D&C red 7-Sun) | 0.5% |
| Ethyl-2,4,6-Trimethylbenzoylphenylphosphinate photoinitiator (Lucirin TPO-L-BASF) | 2% |

Nitrocellulose, ethyl acetate and pigment are introduced into a container and placed under stirring with a Rayneri laboratory mixer until a homogeneous mixture is obtained. An aluminum foil will have been previously positioned on the top of the container to prevent the solvents from evaporating. The mixture is then introduced into a Dyno-mill type laboratory bead mill so as to obtain a homogeneous color.

The mixture obtained is then introduced into a light-opaque bottle. The "Ethyl-2,4,6-Trimethylbenzoylphenylphosphinate" photoinitiator is then introduced into the opaque bottle and mixed using a bar magnet for 1 hour. The "Isophorone Urethane Dimethacrylate" and "PEG 400 Extended Urethane Dimethacrylate" compounds are then introduced into the opaque bottle. The mixture obtained is then placed under stirring using a bar magnet for 1 hour.

The surface of the crosslinked coat is not tacky and does not need to be cleaned with isopropanol.

Optionally, the coat may be coated with a finishing layer, with ESSIE "Good to go" composition.

COMPARATIVE EXAMPLES

Each of compositions No. 2 and No. 3 hereinafter is applied to the nails. After drying for approximately 10 minutes, the coats are crosslinked for 60 seconds under the "OPI GelColor" lamp from OPI.

Composition No. 2 (ratio (P1+P2)/P3=5 with 34.5% ethyl acetate)

| | |
|---|---|
| Isophorone Urethane Dimethacrylate (X-851-1066-ESSTECH, Inc.) | 29.40% |
| PEG 400 Extended Urethane Dimethacrylate (X-726-0000-ESSTECH, Inc.) | 19.60% |
| Nitrocellulose with 30% isopropyl alcohol (viscosity: E22-1/2s) | 14% |
| Ethyl acetate | 34.5% |
| Red 7 lacquer (Sunchroma D&C red 7-Sun) | 0.5% |
| Ethyl-2,4,6-Trimethylbenzoylphenylphosphinate photoinitiator (Lucirin TPO-L-BASF) | 2% |

Nitrocellulose, ethyl acetate and pigment are introduced into a container and placed under stirring with a Rayneri laboratory mixer until a homogeneous mixture is obtained. An aluminum foil will have been previously positioned on the top of the container to prevent the solvents from evaporating. The mixture is then introduced into a Dyno-mill type laboratory bead mill so as to obtain a homogeneous color.

The mixture obtained is then introduced into a light-opaque bottle. The "Ethyl-2,4,6-Trimethylbenzoylphenylphosphinate" photoinitiator is then introduced into the opaque bottle and mixed using a bar magnet for 1 hour. The "Isophorone Urethane Dimethacrylate" and "PEG 400 Extended Urethane Dimethacrylate" compounds are then introduced into the opaque bottle. The mixture obtained is then placed under stirring using a bar magnet for 1 hour.

Composition No. 3 (ratio (P1+P2)/P3=2 with 59% butyl acetate)

| | |
|---|---|
| Isophorone Urethane Dimethacrylate (X-851-1066-ESSTECH, Inc.) | 13.5% |
| PEG 400 Extended Urethane Dimethacrylate (X-726-0000-ESSTECH, Inc.) | 9% |
| Nitrocellulose with 30% isopropyl alcohol (viscosity: E22-1/2s) | 16% |
| Butyl Acetate | 59% |
| Red 7 lacquer (Sunchroma D&C red 7-Sun) | 0.5% |
| Ethyl-2,4,6-Trimethylbenzoylphenylphosphinate photoinitiator (Lucirin TPO-L-BASF) | 2% |

Nitrocellulose, butyl acetate and pigment are introduced into a container and placed under stirring with a Rayneri laboratory mixer until a homogeneous mixture is obtained. An aluminum foil will have been previously positioned on the top of the container to prevent the solvents from evaporating. The mixture is then introduced into a Dyno-mill type laboratory bead mill so as to obtain a homogeneous color.

The mixture obtained is then introduced into a light-opaque bottle. The "Ethyl-2,4,6-Trimethylbenzoylphenylphosphinate" photoinitiator is then introduced into the opaque bottle and mixed using a bar magnet for 1 hour. The "Isophorone Urethane Dimethacrylate" and "PEG 400 Extended Urethane Dimethacrylate" compounds are then introduced into the opaque bottle. The mixture obtained is then placed under stirring using a bar magnet for 1 hour.

After drying for 10 min followed by crosslinking for 60 seconds under the "OPI Gelcolor" lamp, the films from both comparative compositions No. 2 and No. 3 above have a tacky surface.

The invention claimed is:

1. A photocrosslinkable cosmetic composition . . . wherein the ratio of the total mass of P1 and P2 to the total mass of P3 is between 0.5 and 2.0.

2. The composition according to claim 1, further comprising a coloring agent chosen from the group consisting of soluble dyes, pigments, nacres and glitter.

3. The composition according to claim 1, wherein said composition further comprises a (meth)acrylate monomer, wherein the proportion of the (meth)acrylate monomer is less than or equal to 10% by weight in relation to the total weight of said composition.

4. The composition according to claim 1, comprising from 10% to 15% by weight of said at least one photocrosslinkable urethane (meth)acrylate compound P1 in relation to the total weight of said composition.

5. The composition according to claim 1, comprising from 5% to 10% by weight of said at least one photocrosslinkable urethane dimethacrylate compound P2 comprising a poly (ethyleneglycol) chain in relation to the total weight of said composition.

6. A kit comprising:
the photocrosslinkable cosmetic composition according to claim 1,
an abrasive material having a granulometry greater than or equal to 200 pm, and
a LED lamp or an UV lamp.

7. A makeup and/or care method of a nail and/or false nail, comprising the following steps:
a) applying, onto a nail or a false nail, the photocrosslinkable cosmetic composition according to claim 1, whereby a coat consisting of at least one layer of said photocrosslinkable cosmetic composition is deposited, and
b) exposing the coated nail or false nail obtained following step a) to UV or visible light radiation, whereby the photocrosslinking of the photocrosslinkable compounds PI and P2 of said composition is carried out.

8. A makeup and/or care method of a nail and/or false nail, comprising the following steps:
i) rubbing the surface of a nail or false nail with an abrasive material having a granulometry greater than or equal to 200 pm,
ii) applying the photocrosslinkable cosmetic composition according to claim 1 onto the surface of the nail or false nail which has been rubbed following step i), whereby a coat consisting of at least one layer of said photocrosslinkable cosmetic composition is deposited, and iii) exposing the coated nail or false nail obtained following step ii) to a LED lamp or an UV lamp, whereby the photocrosslinking of the photocrosslinkable cosmetic composition is carried out.

\* \* \* \* \*